United States Patent
Pinhas

[11] 3,979,456
[45] Sept. 7, 1976

[54] PHENOXYALKYLAMINES, PROCESS FOR THEIR PREPARATION AND APPLICATIONS THEREOF

[75] Inventor: Henri Pinhas, Paris, France

[73] Assignee: Laboratoires Laroche Navarron, Levallois, France

[22] Filed: Jan. 20, 1975

[21] Appl. No.: 542,227

Related U.S. Application Data

[62] Division of Ser. No. 210,107, Dec. 20, 1971, Pat. No. 3,873,620.

[30] Foreign Application Priority Data

Dec. 28, 1970. France .............................. 70.46875

[52] U.S. Cl. .................. 260/570.7; 260/348 R; 260/501.18; 260/501.19; 260/566 F; 260/570 R; 260/570.6; 260/570.8 R; 260/590 D; 260/591; 260/612 R; 424/316; 424/330

[51] Int. Cl.² ........................................ C07C 93/06

[58] Field of Search .................. 260/570.7, 501.18; 424/330

[56] References Cited
UNITED STATES PATENTS

| | | | |
|---|---|---|---|
| 3,410,901 | 11/1968 | Kunz et al. .................. | 260/501.17 X |
| 3,501,769 | 3/1970 | Crowther et al. .............. | 260/501.17 |
| 3,641,152 | 2/1972 | Shavel, Jr. et al. ............ | 260/570.7 |
| 3,646,067 | 2/1972 | Narayanan et al. .......... | 260/570.7 X |
| 3,857,891 | 12/1974 | Holmes et al. ............. | 260/501.18 X |

*Primary Examiner*—Robert V. Hines
*Attorney, Agent, or Firm*—Oldham & Oldham Co.

[57] ABSTRACT

This invention relates to phenoxyalkylamines having the formula:

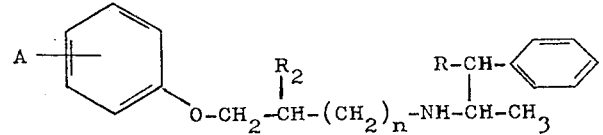

in which $n$ is zero or 1, R is hydrogen or a hydroxy group, $R_2$ is hydrogen, a hydroxy group or an alkyl group, $R_2$ being other than hydroxy when $n$ is zero, A is a group

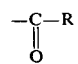

or

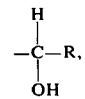

$R_1$ being hydrogen, a cycloalkyl group or an aryl group.

Said phenoxyalkylamines possess coronary vasodilatator and cardiotonic properties.

3 Claims, No Drawings

PHENOXYALKYLAMINES, PROCESS FOR THEIR PREPARATION AND APPLICATIONS THEREOF

This is a division of application Ser. No. 210,107, filed Dec. 20, 1971 and now U.S. Pat. No. 3,873,620.

The present invention relates to phenoxyalkylamines, to processes for their preparation an to the applications thereof, particularly in human medicine.

There is already known a therapeutic composition useful in particular as coronary vasodilatator and as antispasmodic drug, comprising, as active ingredient, a phenoxyalkylamine having the formula:

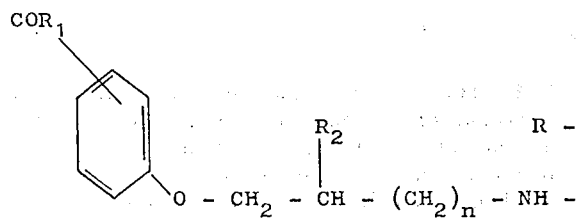

in which $n$ is zero or 1, R is hydrogen or a hydroxy group, $R_1$ is an alkyl group and $R_2$ is hydrogen, a hydroxy group or an alkyl group, $R_2$ being other than hydroxy when $n$ is equal to zero, or a product resulting from hydrogenation of the ketone group $COR_1$ thereof to an alcohol group $CHOHR_1$.

The vasodilatator and spasmolytic properties of said prior phenoxyalkylamines were found to be quite outstanding;

However, there have been found new phenoxyalkylamines which, while having still better vasodilatator and spasmolytic properties than those — although already exceptional — of the prior phenoxyalkylamines, have a better therapeutic ratio than the latter. Phenoxyalkylamines were prepared which exhibit toxicity only at dosages above 500 mg and sometimes up to 1500 mg under the same experimental conditions as those mentioned above.

Said new phenoxyalkylamines according to the invention have the formula:

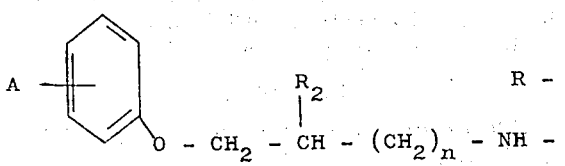

in which $n$ is zero or 1, R is hydrogen or a hydroxy group, $R_2$ is hydrogen, a hydroxy or alkyl group, $R_2$ being other than hydroxy when $n$ is zero, A is a group

or

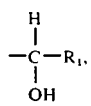

$R_1$ being hydrogen, a cycloalkyl group or an aryl group.

In the above definition, the alkyl radicals are advantageously lower radicals, having typically from 1 to 12 carbon atoms and preferably from 1 to 6 carbon atoms.

When $R_1$ is an aryl group, it is advantageously a phenyl group, while the preferred cycloalkyl ring is cyclohexyl.

The phenoxyalkylamines of this invention may also exist in the form of acid addition salts thereof with inorganic or organic acids and typically as the hydrohalides, particularly the hydrochlorides and hydrobromides, as the nitrates, sulfates, methanesulfonates, lactates, citrates, maleates, tartrates, acetylsalicylates, acetates, oxalates, and the like salts which are readily prepared by reacting compounds (I) as the free base with stoichiometrically equivalent amounts of the selected acid or acids.

Formula (I) always includes at least one asymmetrical carbon atom. It is understood that the invention includes within its scope the optically active and racemic forms of the phenoxyalkylamines having the formula (I).

To prepare said phenoxyalkylamines, an amine of the formula:

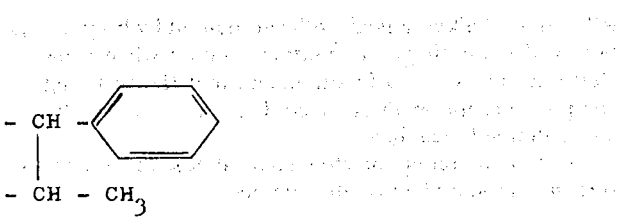

(I)

is condensed with a phenoxy intermediate having the formula:

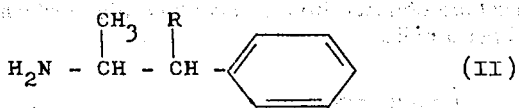

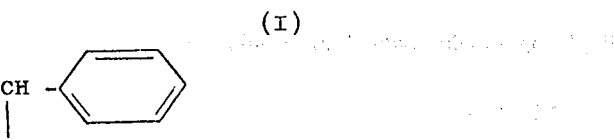

in which Z is a radical selected from the radicals

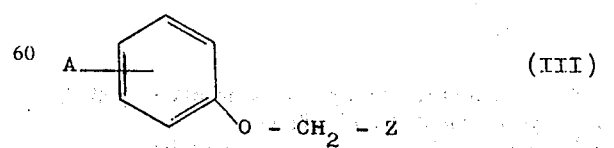

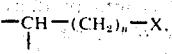

X being a halogen atom and R′₂ being a hydrogen atom or an alkyl radical,

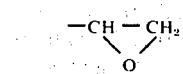

and

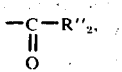

R″₂ being an alkyl radical, with subsequent hydrogenation of the resulting condensation product when it includes a double bond in the chain, and the resulting compound is optionally reduced, R, A and n having the above-defined meanings.

The ultimate reduction step makes it possible to convert the ketonic phenoxyalkylamines

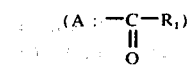

if desired, to the alcoholic phenoxyalkylamines

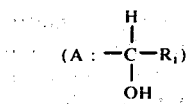

The phenoxyalkylamines (I) in which R₂ is hydrogen are obtained from compounds (III) in which Z is a radical —CH₂—(CH₂)ₙ—X.

The phenoxyalkylamines (I) in which R₂ is an alkyl radical are obtained from compounds (III) in which Z is either a radical

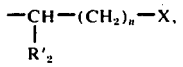

R′₂ being an alkyl radical, or a radical

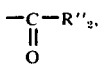

it being understood that in the latter case it is convenient to reduce suitably the double bond formed in the chain.

When group Z represents the group

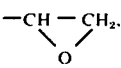

the condensation reaction gives rise to phenoxyalkylamines hydroxylated in their chain.

It is generally advantageous to conduct the condensation under refluxing conditions within an alcohol solvent, e.g. within ethanol in the presence of triethylamine or other basic agents. When intermediate (III) possesses a ketone function in the side-chain, it is preferred to use a benzene solvent and to remove the water formed during the condensation. In the latter case, the double bond formed in the chain may then be saturated by means of a mild reduction, for example by the catalytic route in the presence of palladium-on-charcoal to give compounds (I) in which A is ketonic.

Whether such ketonic compounds are obtained directly by condensation or are derived from a condensation followed by a reduction, as explained above, they may be reduced to their alcoholic homologs

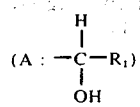

by the catalytic route, typically in the presence of platinum oxide or other metal catalysts, and preferably with a metal borohydride such as sodium or potassium borohydride, within an alcohol solvent such as methanol.

When the condensation products unsaturated in the chain are reduced with a borohydride, not only is the double bond reduced, but also the ketone function included in A, so that the alcoholic phenoxyalkylamines are obtained directly.

Intermediates (III) are obtained by reacting a phenol compound of the formula:

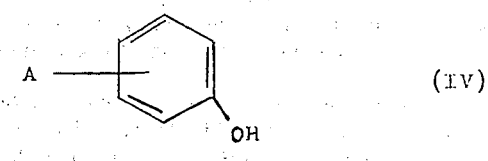

with a halogenated compound:

Y being halogen and the other symbols having the aforementioned meanings.

This reaction is preferably carried out under refluxing conditions in water, in the presence of a stoichiometric amount of a metal hydroxide, typically sodium hydroxide which binds the hydrohalic acid released.

The following examples illustrate the invention.

EXAMPLE 1

4-[2-(α-methyl-phenethylamino)-ethoxy]cyclohexanophenone $A = COR_1 = -CO-C_6H_{11}; R = R_2 = H; n = 0$ a. 4-(2-bromo-ethoxy)-cyclohexanophenone is first prepared: p-hydroxy-cyclohexanophenone (0.5 mole) is dissolved in water (700 ml) containing sodium hydroxide (0.5 mole). 1,2-dibromo-ethane (0.6 mole) is added to the refluxing solution.

The solution is refluxed during 20 hours, and is then allowed to cool. It is extracted with diethyl ether, and is then washed with dilute sodium hydroxide and then with water.

The ether phase is dried, concentrated, and the residue is then distilled:

b.p.$_{0.5}$ = 202°–206°C  M.p. = 58°–60°C  Yield = 60 %.

2-(2-bromo-ethoxy)-cyclohexanophenone is prepared using the above procedure:

b.p.$_{0.5}$ = 190°–195°C  Yield = 25 %.

b. A solution of α-methyl-phenethylamino (1 mole), 4-(2-bromo-ethoxy)-cyclohexanophenone (1 mole) and triethylamine (3 moles) in ethanol (600 ml) is refluxed during 48 hours. The solvent is removed in vacuo. The residue is dissolved in an organic solvent (such as diethyl ether or ethyl acetate). A 10 % hydrochloric acid solution is added with vigorous stirring. The crystals are suction filtered and are then recrystallized from methanol (Yield 75 %) to give 4-[2-(α-methyl-phenethyl-amino)-ethoxy]-cyclohexanophenone hydrochloride, m.p. = 177°–179°C.

The procedure described above is used with the ortho derivative, to give 2-[2-(α-methyl-phenethylamino)-ethoxy]-cyclohexanophenone, m.p. 160°–162°C. Yield = 60 %.

EXAMPLE 2

$A = -CO-C_6H_{11}; R = OH; R_2 = H; n = O$

4-[2-(β-hydroxy-α-methyl-phenethylamino)-ethoxy]-cyclohexanophenone and its hypochloride are prepared as described above, except for the difference that α-methyl-phenethylamine is substituted with β-hydroxy-α-methyl-phenethylamine. The yield is 70 % and the hydrochloride melts at 170°–172°C.

EXAMPLE 3

1-[(1-cyclohexyl-1-hydroxy)-methyl]-4-[2-(α-methyl-phenethylamino) -ethoxy]-benzene and its hydrochloride:

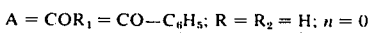

Potassium borohydride (0.12 mole) is gently added to 4-[2-α-(methyl-phenethylamino)-ethoxy]-cyclohexanophenone (0.1 mole) dissolved in 90 % methanol (150 ml), at a temperature below 0°C.

After 15 hours, the methanol is removed at 20°–30°C, in vacuo. The residue is taken up into water and ether. The organic phase is thoroughly washed with water. The ether phase is dried and evaporated. The residue is converted to the hydrochloride, in the usual manner.

The white crystals recrystallize from alcohol/ether. M.p. = 174°–175°C   Yield = 90 %.

EXAMPLE 4

4-[2-(α-methyl-phenethylamino)-ethoxy]-benzophenone.

$A = COR_1 = CO-C_6H_5; R = R_2 = H; n = 0$ a. 4(2-bromo-ethoxy)-benzophenone is first prepared from para-hydroxy-benzophenone and 1,2-dibromo-ethane, using the same procedure as in example 1.

$b.p._{0.5}$ = 185°–190°C   m.p. = 52°C.

b. A solution of α-methyl-phenethylamine (1 mole), 4-(2-bromo-ethoxy)-benzophenone (1 mole) and triethylamine (3 moles) in ethanol (600 ml) is refluxed during 48 hours. Treatment is described in example 1 gives 4-[2-(α-methyl-phenethylamino)-ethoxy]-benzophenone hydrochloride (68 %). M.p. 174°–176°C.

EXAMPLE 5

1-[α-hydroxy-benzyl]-4-[2-(α-methyl-phenethylamino)-ethoxy]-benzene and its hydrochloride.

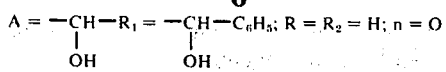

4-[2-(α-methyl-phenethylamino)-ethoxy]-benzophenone is reduced in the usual manner with potassium borohydride.

Treatment as in example 1 gives 1-[α-hydroxy-benzyl]-4[2-(α-methyl-phenethylamino)-ethoxy]-benzene hydrochloride (92 %); m.p. = 165°–168°C.

EXAMPLE 6

4-[2-hydroxy-3-(α-methyl-phenethylamino)-propioxy]-cyclohexanophenone.

$A = CO-C_6H_{11}; n = 1; R_2 = OH; R = H$ 4-(2,3-epoxy-propoxy)-cyclohexanophenone is first prepared. For this purpose, para-hydroxy-cyclohexanophenone (0.1 mole) is dissolved in 5 % sodium hydroxide (0.1 mole); 1-chloro-2,3-epoxy-propane (0.11 mole) is added to the stirred solution, over 1 hour.

After 24 hours, the resulting cyrstals are suction filtered, and are then washed with water and dried.

The residue is distilled: $b.p._{0.5}$ = 180°–186°C; yield = 70 %.

α-methyl-phenethylamine (0.1 mole) and 4-(2,3-epoxy-propoxy)-cyclohexanophenone (0.1 mole) are then refluxed during four hours in 90 % alcohol (100 ml). The solvent is removed in vacuo. The residue is taken up into diethyl ether. 5 % hydrochloric acid in then added thereto. 4[2-hydroxy-3-(α-methyl-phenethylamino)-propoxy]-cyclohexanophenone precipitates out on vigorous stirring. It is recrystallized from ethanol. M.p. 174°–177°C.

EXAMPLE 7

The ketone function of the above described product (example 6) is reduced with borohydride, in the usual manner, to give 1-[(1-cyclohexyl-1-hydroxy)-methyl]-4-[2-hydroxy-3-(α-methyl-phenethylamino)-propoxy]-benzene hydrochloride. M.p. 130°–136°C.

EXAMPLE 8

4[2-(α-methyl-phenethylamino)-propoxy]-cyclohexanophenone.

$A = CO-C_6H_{11}; R_2 = CH_3; n = 0; R = H$ para-Hydroxy-cyclohexanophenone (0.1 mole) and sodium hydroxide (0.1 mole) are dissolved in 80 % alcohol (100 ml).

Chloroacetone (0.12 mole) is added dropwise to this solution.

After refluxing during 7 hours, the reaction mixture is concentrated in vacuo. It is then extracted with ether, washed with 5 % sodium hydroxide and then with water.

The residue is then distilled: $b.p._{0.5}$ = 182°–187°C. Yield = 72 %.

4-(2-oxo-propoxy)-cyclohexanophenone (0.02 mole) and α-methyl-phenethylamine (0.02 mole) are then heated in benzene solution. The water formed is removed by means of a Dean-Stark apparatus.

The solvent is removed in vacuo and the residue is hydrogenated in the presence of 5 % palladium-oncharcoal, in alcohol solution, at room temperature, under 2 kg hydrogen pressure.

The alcohol is removed. The residue is taken up into ether, and abundantly washed with water. The ether phase is dried and then concentrated, after which the hydrochloride is prepared. M.p. 130°–134°C.

EXAMPLE 9

1-hydroxymethyl-4-[2-(α-methyl-phenethylamino)-ethoxy]-benzene.

$A = -CH_2OH; R_2 = R = H; n = 0$ 4-(2-bromo-ethoxy)-1-hydroxymethyl-benzene is first prepared from 4-hydroxymethyl-phenol and 1,2-dibromoethane, using the same procedure as in example 1. This bromo derivative is then condensed with α-methyl-phenethylamine, to give 1-hydroxymethyl-4-[2-(α-methyl-phenethylamino)-ethoxy]-benzene hydrochloride in a 50 % yield. M.p. 136°–138°C.

The results of toxicological and pharmacological tests demonstrating the safe character and the activity of the phenoxyalkylamines of this invention are given below.

I - ACUTE TOXICITY

The acute toxicities of said materials were investigated orally, in Swiss mice and Sprague Dawley rats.

The animals are fasted eighteen hours prior to the single administration of the product and are kept under supervision forteen days during which their behavior and death rate were noted.

The $LD_{50}$ of said products, investigated in both species and calculated according to the method according to Litchfield and Wilcoxon are of the order of from 500 to 1500 mg/kg.

II — CORONARY DILATATOR ACTION

1. On the isolated heart — Langendorff's method

The tests were carried out on the hearts of Fauve de Bourgogne (about 2 kg) rabbits. The hearts are rapidly taken out and maintained in surviving condition by perfusion of a physiological (Tyrode type) liquid heated at 37°C and oxygenated under a constant pressure of 50–60 cm of water. Perfusion of the hearts was effected countercurrently, and volumetric determinations of the coronary rate of flow were recorded at 30 second intervals.

After stabilization of the basic rate of flow, the products, dissolved in physiological saline solution, are injected in a volume of from 0.05 to 0.2 ml.

The products produce a marked increase of the coronary rate of flow which is apparent at a dosage of 10 γ; a 50 % increase of the original rate of flow is obtained, depending on the test products, at a dosage comprised within the range from 15 γ to 100 γ.

2. On the whole animal

The tests were carried out in male and female dogs having a weight between 10 and 15 kg.

After chloralose-induced anesthesia, the animals are placed under artificial respiration.

The carotid pressure is recorded, together with the cardiac frequency and the electrocardiogram.

The coronary flux is investigated by means of a nycotron.

The test materials were dissolved in physiological saline solution and administrated by the intravenous route.

Increase of the coronary flux is observed at dosages from 0.5 to 2 mg/kg.

III. ACTION ON CONTRACTILE STRENGTH

The tests were carried out either in the whole animal, or in the isolated heart.

Dogs, both male and female, are anesthetized with chloralose.

Systemic blood pressure is recorded at the level of the carotid with an electric sensor.

The contractile strength of the heart was measured with a strain gauge attached to the wall of the right ventricle.

The products, dissolved in physiological saline solution, are administrated intravenously (external saphenous vein).

The phenoxyalkylamines of this invention produce an increase of the contractile strength of the heart which becomes more marked with time. Generally, this action has a duration of over one hundred minutes. The cardio-tonic action is apparent at dosages from 0.5 to 2 mg/kg.

The products were tested on the isolated heart of rabbit maintained in surviving condition by Langendorff's method. The contractile strength is measured by means of a strain gauge attached to the right ventricle. Cardiac stimulation is apparent at dosages of about 200 γ.

IV. SPASMOLITIC ACTION

The spasmolytic action was studied in vitro with a fragment of duodenum of rat maintained in surviving condition in an oxygenated physiological liquid. Inhibition of 50 % of the contraction due to effusion of a given dose of acetylcholine and barium was studied. The $ED_{50}$ of the test products is comprised within a range from 20 to 65 γ with respect to acetylcholine-induced contraction, and within a range from 15 to 80 γ with respect to barium-induced contraction.

It is apparent from such tests that the phenoxyalkylamines of this invention and their non-toxic salts are useful in human therapeutics for the curative or preventive treatment of heart conditions, as coronary vasodilatator, cardiotonic and spasmolytic drug.

In such applications, the therapeutic composition is advantageously administered orally, at a dosage of from 150 to 750 mg of active ingredient per 24 hours.

Any formulations suitable for this route of administration may be used, the active ingredient being admixed with a pharmaceutically acceptable carrier or excipient.

An example of such a formulation is given:

Tablets containing each: 50 mg (average dose)
 100 mg (strong dose)
Excipients: Talc
 Lactose
 Mg stearate, q.s. to make 1 tablet.

Having now described my invention what I claim and desire to secure by Letters Patent is:

1. A compound selected from the group consisting of phenoxyalkylamines of formula:

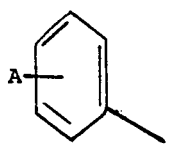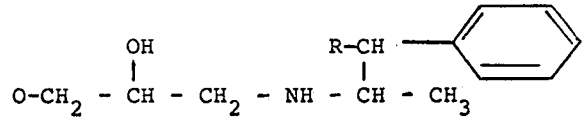

in which R is selected from the group consisting of hydrogen and hydroxy and A is selected from the group consisting of the radicals

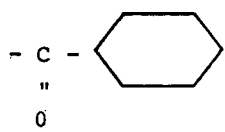 and 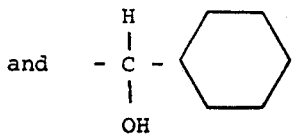

and their non-toxic acid addition salts.

2. 4[2-hydroxy-3(α-methyl-phenethylamino)-propoxy] cyclohexanophenone and its non-toxic acid addition salts.

3. 1-[1-cyclohexyl-1-hydroxy)-methyl] 4-[2-hydroxy-3(α-methyl-phenethyl amino)-propoxy] benzene and its non-toxic acid addition salts.

* * * * *